US 11,493,566 B2

(12) United States Patent
Lacouture

(10) Patent No.: US 11,493,566 B2
(45) Date of Patent: Nov. 8, 2022

(54) ELECTRIC CURRENT IMAGING SYSTEM

(71) Applicants: TEXAS TECH UNIVERSITY SYSTEM, Lubbock, TX (US); Shelby Lacouture, Lubbock, TX (US)

(72) Inventor: Shelby Lacouture, Lubbock, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 128 days.

(21) Appl. No.: 16/328,839

(22) PCT Filed: Sep. 6, 2017

(86) PCT No.: PCT/IB2017/055378
§ 371 (c)(1),
(2) Date: Feb. 27, 2019

(87) PCT Pub. No.: WO2018/047083
PCT Pub. Date: Mar. 15, 2018

(65) Prior Publication Data
US 2019/0187223 A1    Jun. 20, 2019

Related U.S. Application Data

(60) Provisional application No. 62/384,260, filed on Sep. 7, 2016.

(51) Int. Cl.
*G01R 33/02* (2006.01)
*G01R 19/00* (2006.01)
(52) U.S. Cl.
CPC ..... *G01R 33/0206* (2013.01); *G01R 19/0092* (2013.01); *G01R 33/02* (2013.01)

(58) Field of Classification Search
CPC . G01R 19/0092; G01R 33/02; G01R 33/0206
See application file for complete search history.

(56) References Cited

U.S. PATENT DOCUMENTS 4,623,842 A   11/1986   Bell et al.
5,073,858 A * 12/1991   Mills ................... G01R 33/16
                                                    600/410

(Continued)

OTHER PUBLICATIONS

Shiraishi, K., et al. "Visualization of current vectors in multi-layered printed circuit board." Proc. 10th Int. Symp. Flow. Visualization—ISFV, 2002., heretofore referred to as Shiraishi (Year: 2002).*

(Continued)

*Primary Examiner* — Son T Le
*Assistant Examiner* — Adam S Clarke
(74) *Attorney, Agent, or Firm* — Loza & Loza, LLP; Kevin L. Soules

(57) ABSTRACT

An electric current imaging system, device, and method includes an array of vector magnetometers that senses one or more magnetic fields in three directions produced by a flow of electric current. Such a system (and devices and methods thereof) can further include a display that displays a visual reconstruction of the original electric current that produced the magnetic field(s). The disclosed embodiments image electric current flow (both magnitude and direction) without the need for rastering or relative motion between the sensors and the conductor/device being viewed. Such embodiments can be scaled to fit both large and small applications by using discreet devices or manufacturing a single, miniaturized array with MEMS technologies.

20 Claims, 2 Drawing Sheets

(56) References Cited

U.S. PATENT DOCUMENTS

| | | | |
|---|---|---|---|
| 5,170,566 | A | 12/1992 | Fowler et al. |
| 7,408,343 | B2 | 9/2008 | Dmytriw et al. |
| 7,839,409 | B2 | 11/2010 | Noorbakhsh et al. |
| 8,898,358 | B2 | 11/2014 | DeCesaris et al. |
| 8,909,844 | B2 | 12/2014 | DeCesaris et al. |
| 9,638,780 | B2 | 5/2017 | Ookawa |
| 2004/0077964 | A1 | 4/2004 | Nakai |
| 2004/0207396 | A1* | 10/2004 | Xiao ............... G01Q 10/04 324/244 |
| 2005/0108454 | A1 | 5/2005 | Baker et al. |
| 2006/0174044 | A1 | 8/2006 | Bomhoff et al. |
| 2007/0108975 | A1* | 5/2007 | Desplats ............ G01R 33/02 324/247 |
| 2008/0201511 | A1 | 8/2008 | Deshpande et al. |
| 2009/0316029 | A1* | 12/2009 | Hagihara ............ H04N 5/357 348/294 |
| 2010/0237858 | A1* | 9/2010 | Hokari ............. G01R 33/032 324/244.1 |
| 2011/0315880 | A1 | 12/2011 | Nemirovsky |
| 2012/0311211 | A1 | 12/2012 | Gao |
| 2012/0313723 | A1 | 12/2012 | Rofougaran et al. |
| 2013/0229173 | A1* | 9/2013 | Bertrand ........... G01R 33/028 324/225 |
| 2019/0246939 | A1* | 8/2019 | Abe ............... G01R 33/035 |

OTHER PUBLICATIONS

International Search Report and Written Opinion, PCT/IB2017/055378, 8 pages (dated Dec. 30, 2019).
$I^2C$ (Inter-Integrated Circuit), https://en.wikipedia.org/wiki/I$^2$C, downloaded Aug. 31, 2016.
TMS470R1x Inter-Integrated Circuit (I2C) Reference Guide, Texas Instruments, Dallas, Texas, Feb. 2005.
W G Jenks, S S H Sadeghi & JP Wikswo Jr, "SQUIDs for nondestructive evaluation", J. Phys. D: Appl. Phys.30(1997) 293-323.
Ali Sophian & Mengbao Fan, "Pulsed Eddy Current Nondestructive Testing and Evaluation: A Review", Chinese Journal of Mechanical Engineering, Apr. 2017, DOI: 10.1007/s10033-017-0122-4.
International Patent Application No. PCT/IB2017/055378, International Preliminary Report on Patentability and Written Opinion, 12 pages (dated Jan. 28, 2020).

* cited by examiner

ELECTRIC CURRENT IMAGING SYSTEM

CROSS-REFERENCE TO PATENT APPLICATION

This national stage patent application claims priority to International Patent Application No. PCT/IB2017/055378, which was filed under the PCT (Patent Cooperation Treaty) with an international filing date of Sep. 6, 2017, and claims a right of priority under 35 U.S.C. § 365(b) and the benefit under 35 U.S.C. § 119(a) to U.S. Provisional Patent Application Ser. No. 62/384,260 entitled "Electric Current Imaging System" filed on Sep. 7, 2016. The entire contents of U.S. Provisional Patent Application Ser. No. 62/384,260 and International Patent Application No. PCT/IB2017/055378 are hereby incorporated by reference.

TECHNICAL FIELD

Embodiments are related to imaging devices, systems, and methods Embodiments are also related to the imaging of electric current flow. Embodiments further relate to an array of vector magnetometers utilized to image electric current flow.

BACKGROUND

An electric current is a flow of electric charge. In electric circuits, moving electrons in wires often carry these electric charges. Moving electronics can also be carried by ions in an electrolyte, or by both ions and electrons such as in plasma. Currently, there is no known device capable of imaging electric current. Current attempts at imaging electric current require relative motion between the current flow and a sensor to build up an image bit by bit.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is therefore one aspect of the disclosed embodiments to an improved imaging device, system, and method.

It is another aspect of the disclosed embodiments to provide for an apparatus, system, and method for the imaging of electric current flow.

It is also an aspect of the disclosed embodiments to provide for an array of vector magnetometers utilized to image electric current flow.

It is yet another aspect of the disclosed embodiment to provide for a system, method, and system for imaging electric current flow (both magnitude and direction) without the need for rastering or relative motion between the sensors and the conductor/device being viewed.

The aforementioned aspects and other objectives and advantages can now be achieved as described herein. An electric current imaging system is disclosed, which includes an array of vector magnetometers that senses at least one magnetic field in three directions produced by a flow of electric current. Such a system further includes a display that displays a visual reconstruction of an original electric current that produces the at least one magnetic field.

Such a system can image electric current flowing in a conductor, device, or on a circuit board. The system can reproduce a visual image of the electric current flow as lines or vectors representing both direction and magnitude in much the same way that a thermal imager visualizes heat. The array of vector magnetometers can sense the magnetic field(s) produced by a flow of electric current, and through the application of Ampere's Law and Biot-Savart Law, to reconstruct visually the original electric current producing the magnetic field(s).

Because a vector magnetometer senses all three components of a magnetic field at a point in space, a large array of the units can reproduce with relatively good resolution a "picture" of the electric current flow. Additionally, because all three axes are sensed, even the flow of electric current at a distance can be constructed including magnitude because triangulation of a magnetic field's source is possible. The components used for the vector magnetometers that constitute the sensing array are capable of sensing a magnetic field in three dimensions and have a sufficient sensitivity to measure the required level of magnetic field produced (i.e., they are sensitive enough).

Thus, in one example embodiment an electric current imaging system can be implemented, which includes an array of vector magnetometers that senses one or more magnetic fields in three directions produced by the flow of electric current. Such a system can further include a display that displays a visual reconstruction of the original electric current that produced the one or more magnetic fields.

In other example embodiments, the flow of electric current can be reconstructed at a distance including a magnitude. In another example, the array of vector magnetometers can include a group of sensing elements. A sensor is therefore provided, which includes the array of magnetometers. Note that in some example embodiments, such a sensor can communicate information via digital communications such as, for example, an $I^2C$ (Inter-Integrated Circuit) protocol. In some example embodiments, such a sensor can be a 3D vector magnetometer sensor.

In yet another example embodiment, the aforementioned system can include a microprocessor that initializes the sensing elements. In addition, a reconstruction module can be provided, which visually reconstructs the flow of the electric current from data detected by the array of magnetometers.

In some example embodiments, the aforementioned array of vector magnetometers can include a MEMS array of vector magnetometer structures configured on a single IC (Integrated Circuit) chip. In some example embodiments, the MEMS array can be mated with a CMOS (Complementary Metal Oxide Semiconductor) VLSI (Very Large Scale Integrated Circuit) to perform demultiplexing and readout functions. In still other example embodiments, the aforementioned CMOS VLSI can be configured as a CMOS readout IC and/or a CCD (Charged Coupled Device).

In another example embodiment, an electric current imaging method can be implemented, which includes, for example, steps or operations such as sensing with an array of vector magnetometers at least one magnetic field in three directions produced by a flow of electric current; and displaying a visual reconstruction of an original electric current the produces the at least one magnetic field. The flow of the electric current can be reconstructed at a distance including a magnitude, and as indicated previously, the array of vector magnetometers can include a group of sensing elements. In addition, a step or operation can be implemented in which a microprocessor initializes the sensing elements. In still other embodiments, a step or operation can be implemented to visually reconstruct the flow of the electric current from data detected by the array of magnetometers. This step or operation can be implemented or facilitated by the reconstruction module discussed herein.

In some example embodiments, a step or operation can be implemented in which the array of vector magnetometers is implemented to include a MEMS array of vector magnetometer structures configured on a single IC (Integrated Circuit) chip. In still another example embodiment, a step or operation can be implemented for mating the MEMS array with a CMOS (Complementary Metal Oxide Semiconductor) VLSI (Very Large Scale Integrated Circuit) to perform demultiplexing and readout functions. A step or operation can later be implemented to perform the demultiplexing and readout functions.

BRIEF DESCRIPTION OF THE DRAWINGS

The accompanying figures, in which like reference numerals refer to identical or functionally-similar elements throughout the separate views and which are incorporated in and form a part of the specification, further illustrate the disclosed embodiments and, together with the detailed description of the disclosed embodiments, serve to explain the principles of the present invention.

DETAILED DESCRIPTION

Figure 1:
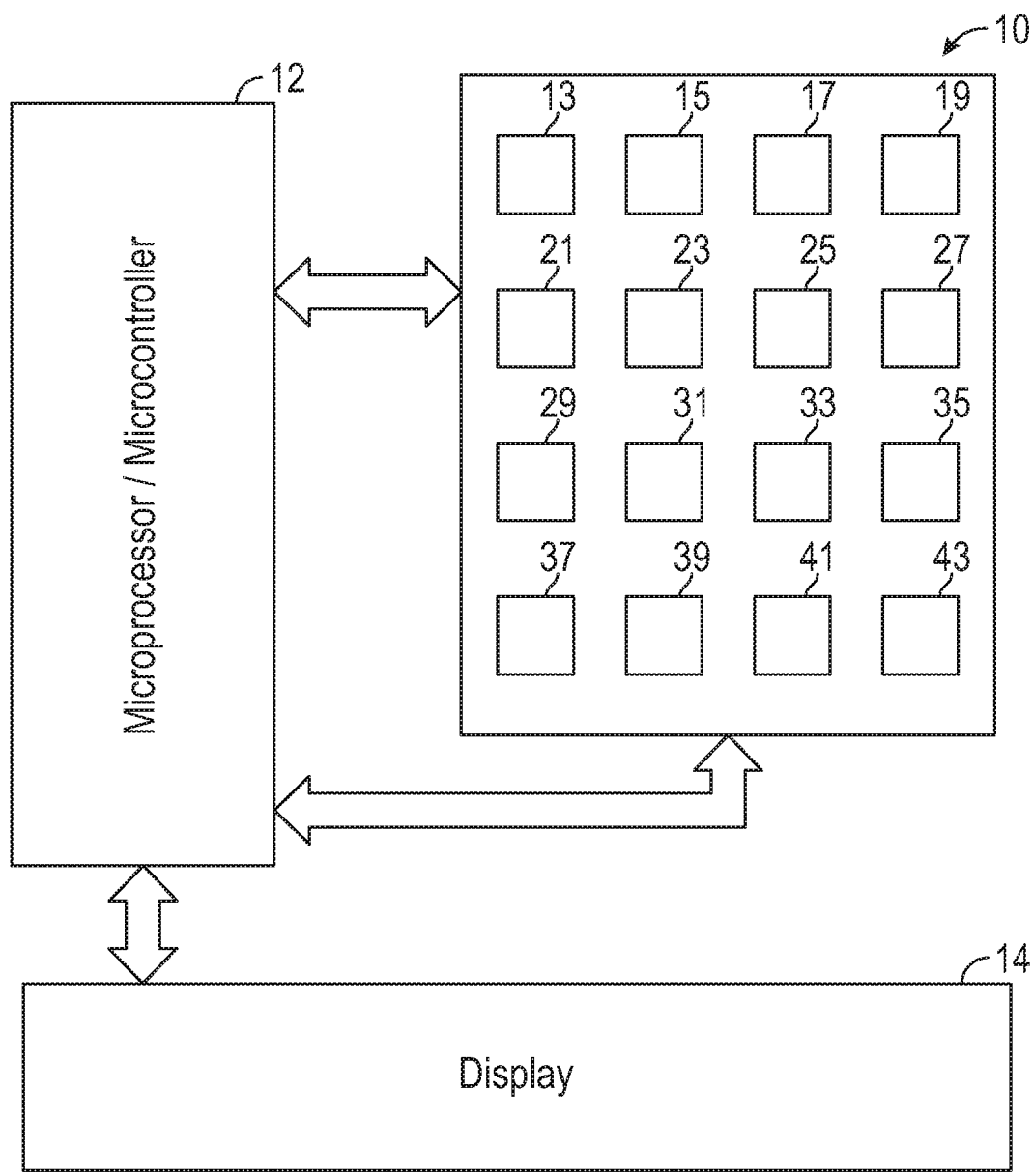
FIG. 1 illustrates a block diagram of an imaging system, in accordance with an example embodiment.

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to identical, like or similar elements throughout, although such numbers may be referenced in the context of different embodiments. As used herein, the term "and/or" includes any and all combinations of one or more of the associated listed items.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms such as "and," "or," or "and/or" as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The disclosed embodiments describe a system, device, and method for imaging electric current flow (both magnitude and direction) without the need for rastering or relative motion between the sensors and the conductor/device being viewed. The disclosed embodiments can be scaled to fit both large and small applications by using discreet devices or manufacturing a single, miniaturized array with MEMs technologies.

FIG. 1 illustrates a block diagram of an imaging system 20, in accordance with an example embodiment. The imaging system 20 includes an array 10 of sensing elements 13, 15, 17, 19, 21, 23, 25, 27, 29, 31, 33, 35, 37, 39, 41, and 43. The configuration depicted in FIG. 1 is illustrated for ease of explanation as a simple 4×4 sensor array of 3D vector magnetometer elements 13, 15, 17, 19, 21, 23, 25, 27, 29, 31, 33, 35, 37, 39, 41, and 43 (e.g., a HMC5983 3D vector magnetometer sensor made by Honeywell). It can be appreciated that although a 4×4 sensor array 10 is shown in FIG. 1, embodiments are not limited to a 4×4 array configuration. That is, arrays of other sizes (e.g., m×m, m×n, etc.) can be implemented in accordance with other embodiments. The particular 4×4 array size depicted in FIG. 1 is discussed herein for illustrative purposes only and should not be interpreted as a limiting feature of the disclosed embodiments.

Each element 13, 15, 17, 19, 21, 23, 25, 27, 29, 31, 33, 35, 37, 39, 41, and/or 43 can sense the magnetic field at that location in space in all three dimensions. The imaging system 20 thus functions as a sensor, which communicates this information (and is set up for varying field magnitudes) via a communications protocol such as, for example, an I²C (Inter-Integrated Circuit) protocol. Note that I²C is a multi-master, multi-slave, single-ended, serial computer bus that can be utilized for attaching lower-speed peripheral ICs (Integrated Circuits) to processors and microcontrollers such as the microprocessor/microcontroller 12 shown in FIG. 1 in short-distance, intra-board communication. The microprocessor and/or microcontroller 12 can initialize, where required, the sensing elements 13, 15, 17, 19, 21, 23, 25, 27, 29, 31, 33, 35, 37, 39, 41, and/or 43 and can utilize a module (e.g., a software module) to reconstruct the electric current flow from this data. This information can then be sent to a display 14 (e.g., a computer screen/monitor) for viewing.

To implement an example embodiment on a much smaller scale, useful for imaging very small surface electric current flows from a conductor or a conducting device, the discreet vector magnetometer in the above example can be replaced by a MEMS fabricated miniaturized array of vector magnetometer structures on a single chip. Such a MEMs array can be constructed and can then be mated with a Complementary Metal Oxide Semiconductor (CMOS) Very Large Scale Integrated Circuit (VLSI) to perform demultiplexing and readout functions in a manner very similar to that used for thermal imaging systems using microbolometer technology. This use of CMOS readout ICs, typically Charged Coupled Device (CCD) technology, greatly simplifies the implementation of very large imaging arrays, allowing versions of the Invention with very high resolution.

Note that in some example embodiments, computer program code for carrying out operations associated with the disclosed embodiments may be written in an object oriented programming language (e.g., Java, C#, C++, etc.). Such computer program code, however, for carrying out operations of particular embodiments can also be written in conventional procedural programming languages, such as the "C" programming language or in a visually oriented programming environment, such as, for example, Visual Basic.

The program code may execute entirely on the user's computer, partly on the user's computer, as a stand-alone software package, partly on the user's computer and partly on a remote computer, or entirely on the remote computer. In the latter scenario, the remote computer may be connected to a user's computer through a local area network (LAN) or a wide area network (WAN), wireless data network e.g., Wi-Fi, Wimax, IEEE 802.xx, and cellular network or the connection may be made to an external computer via most third party supported networks (e.g., through the Internet via an Internet Service Provider).

The embodiments are described at least in part herein with reference to flowchart illustrations and/or block diagrams of methods, systems, and computer program products and data structures according to embodiments of the invention. It will be understood that each block of the illustrations, and combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the various block or blocks, flowcharts, and other architecture illustrated and described herein.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 2:
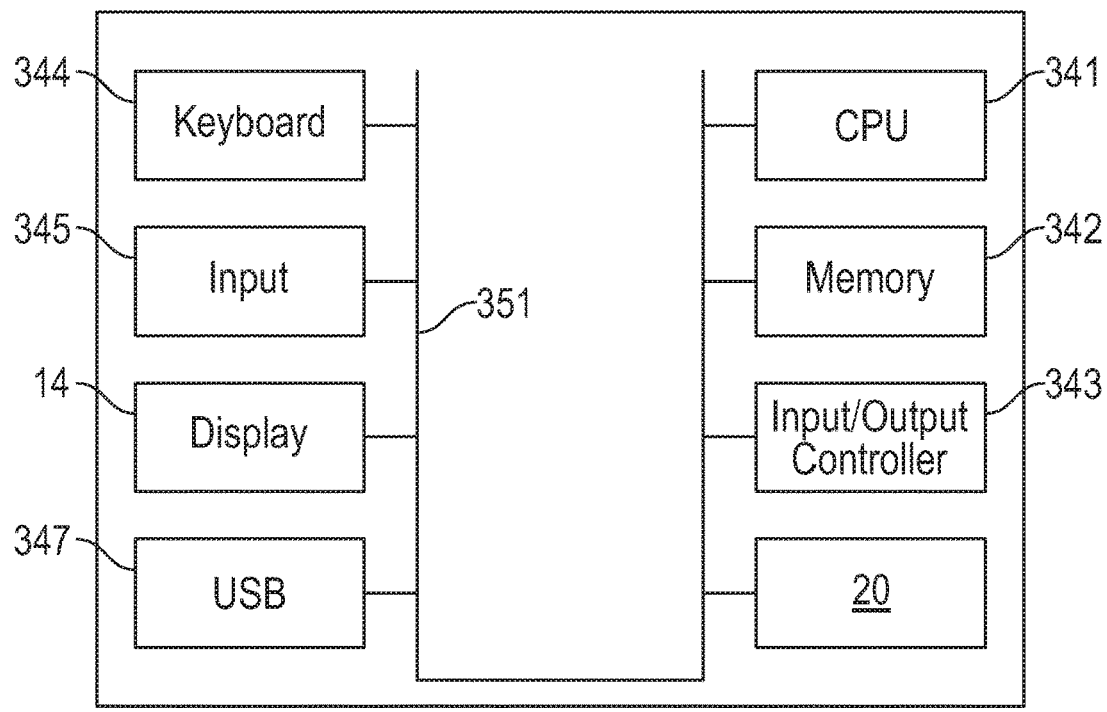
FIG. 2 illustrates a system for data-processing apparatus or system that can be utilized to implement instructions associated with and/or for operating the system depicted in FIG. 1, in accordance with an example embodiment.
Figure 3:
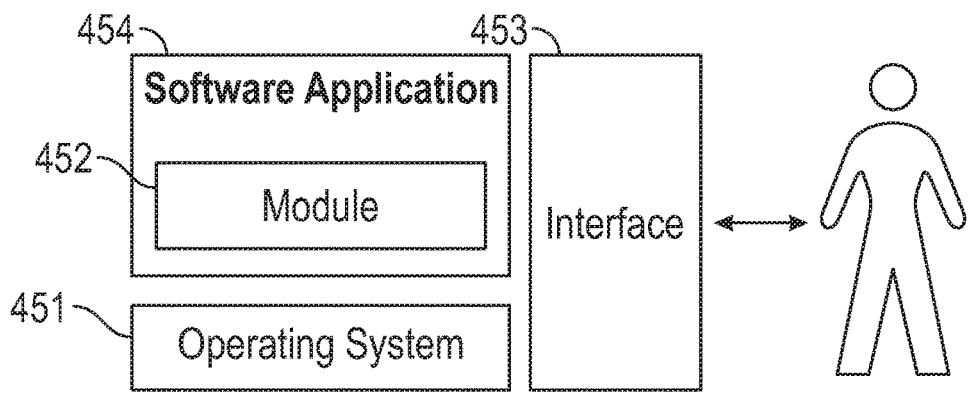
FIG. 3 illustrates a schematic view of a software system including a module, an operating system, and a user interface, in accordance with an example embodiment.

FIG. 2 and FIG. 3 are provided as exemplary diagrams of data-processing environments in which embodiments may be implemented. It should be appreciated that FIG. 2 and FIG. 3 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

As illustrated in FIG. 2, some embodiments may be implemented in the context of a data-processing system 400 that can include one or more processors such as a CPU (Central Processing Unit) 341, a memory 342, a controller 343 (e.g., an input/output controller), a peripheral USB (Universal Serial Bus) connection 347, a keyboard 344 (e.g., a physical keyboard or a touch screen graphically displayed keyboard), an input component 345 (e.g., a pointing device, such as a mouse, track ball, pen device, which may be utilized in association or with the keyboard 344, etc.), the display 14 depicted in FIG. 1, and in some embodiments, the microprocessor/microcontroller 20, which may be implemented in the context of software and/or hardware.

Data-processing system 400 may be, for example, a client computing device (e.g., a client PC, laptop, tablet computing device, etc.), which communicates with peripheral devices (not shown) via a client-server network (e.g., wireless and/or wired). In another embodiment, the data-processing system may be a server in the context of a client-server network or other server-based network implementation.

As illustrated, the various components of data-processing system 400 can communicate electronically through a system bus 351 or other similar architecture. The system bus 351 may be, for example, a subsystem that transfers data between, for example, computer components within data-processing system 400 or to and from other data-processing devices, components, computers, etc. Data-processing system 400 may be implemented as, for example, a server in a client-server based network (e.g., the Internet) or can be implemented in the context of a client and a server (i.e., where aspects are practiced on the client and the server). Data-processing system 400 may be, for example, a stand-alone desktop computer, a laptop computer, a Smartphone, a pad computing device, a server, and so on. In some example embodiments, the data-processing system 400 may implement all or a part of the device/system shown in FIG. 1.

FIG. 3 illustrates a computer software system 450 for directing the operation of the data-processing system 400 shown in FIG. 2. Software application 454 can be stored, for example, in memory 342 of FIG. 2. The computer software system 450 can include a kernel or operating system 451, a shell or interface 453 and the software application 454. One or more application programs, such as the software application 454, may be "loaded" (i.e., transferred from, for example, memory 342 or another memory location) for execution by the data-processing system 400. The data-processing system 400 can receive user commands and data through the interface 453; these inputs may then be acted upon by the data-processing system 400 in accordance with instructions from operating system 451 and/or software application 454. The interface 453, in some embodiments, can serve to display results, whereupon a user may supply additional inputs or terminate a session.

The software application 454 can include one or more modules such as, for example, a module 452 (or a module composed of a group of modules), which can, for example, implement instructions or operations such as those described herein. Examples of instructions that can be implemented by module 452 include the various steps or operations described herein with respect to operations of system 20, which may be stored in memory 342 and processed by, for example, the CPU 341 and/or another processor.

The following discussion is intended to provide a brief, general description of suitable computing environments in which the system and method may be implemented. Although not required, the disclosed embodiments will be described in the general context of computer-executable instructions, such as program modules, being executed by a single computer. In most instances, a "module" constitutes a software application. However, a module may also be composed of, for example, electronic and/or computer hardware or such hardware in combination with software. In some cases, a "module" can also constitute a database and/or electronic hardware and software that interact with such a database.

Generally, program modules include, but are not limited to, routines, subroutines, software applications, programs, objects, components, data structures, etc., that perform particular tasks or implement particular abstract data types and instructions. Moreover, those skilled in the art will appreciate that the disclosed method and system may be practiced with other computer system configurations, such as, for example, hand-held devices, multi-processor systems, data networks, microprocessor-based or programmable consumer electronics, networked PCs, minicomputers, mainframe computers, servers, and the like.

Note that the term module as utilized herein can refer to a collection of routines and data structures that perform a particular task or implement a particular abstract data type. Modules may be composed of two parts: an interface, which lists the constants, data types, variable, and routines that can be accessed by other modules or routines; and an implementation, which is typically private (accessible only to that module) and which includes source code that actually implements the routines in the module. The term module may also simply refer to an application, such as a computer program designed to assist in the performance of a specific task, such as word processing, accounting, inventory management, etc. Thus, the various instructions or steps such as described herein, can be implemented in the context of such a module or modules, sub-modules, and so on.

FIGS. 2-3 are thus intended as examples and not as architectural limitations of disclosed embodiments. Additionally, such embodiments are not limited to any particular application or computing or data processing environment. Instead, those skilled in the art will appreciate that the disclosed approach may be advantageously applied to a variety of systems and application software. Moreover, the disclosed embodiments can be embodied on a variety of different computing platforms, including, for example, Windows, Macintosh, UNIX, LINUX, and the like.

Based on the foregoing, it can be appreciated that a number of embodiments, preferred and alternative, are disclosed herein. For example, in one embodiment, an electric current imaging system can be implemented which includes an array of vector magnetometers that senses at least one magnetic field in three directions produced by a flow of electric current; and a display that displays a visual reconstruction of an original electric current that produces the at least one magnetic field.

In some example embodiments, the flow of the electric current can be reconstructed at a distance including a magnitude. In another example, the array of vector magnetometers can include a group of sensing elements. A sensor is therefore provided which includes the array of magnetometers. Note that in some example embodiments, such a sensor can communicate information via an I$^2$C (Inter-Integrated Circuit) protocol. In some example embodiments, such a sensor can be a 3D vector magnetometer sensor.

In yet another example embodiment, the aforementioned system can include a microprocessor that initializes the sensing elements. In addition, a reconstruction module can be provided, which visually reconstructs the flow of the electric current from data detected by the array of magnetometers.

In some example embodiments, the aforementioned array of vector magnetometers can include a MEMS array of vector magnetometer structures configured on a single IC (Integrated Circuit) chip. In some example embodiments, the MEMS array can be mated with a CMOS (Complementary Metal Oxide Semiconductor) VLSI (Very Large Scale Integrated Circuit) to perform demultiplexing and readout functions. In still other example embodiments, the aforementioned CMOS VLSI can be configured as a CMOS readout IC and/or a CCD (Charged Coupled Device).

In another example embodiment, an electric current imaging method can be implemented, which includes, for example, steps or operations such as sensing with an array of vector magnetometers at least one magnetic field in three directions produced by a flow of electric current; and displaying a visual reconstruction of an original electric current that produces the at least one magnetic field. The flow of the electric current can be reconstructed at a distance including a magnitude, and as indicated previously, the array of vector magnetometers can include a group of sensing elements. In addition, a step or operation can be implemented in which a microprocessor initializes the sensing elements. In still other embodiments, a step or operation can be implemented to visually reconstruct the flow of the electric current from data detected by the array of magnetometers. This step or operation can be implemented or facilitated by the reconstruction module discussed herein.

In some example embodiments, a step or operation can be implemented in which the array of vector magnetometers is implemented to include a MEMS (Micro-Electro-Mechanical Systems) array of vector magnetometer structures configured on a single IC (Integrated Circuit) chip. In still another example embodiment, a step or operation can be implemented for mating the MEMS array with a CMOS (Complementary Metal Oxide Semiconductor) VLSI (Very Large Scale Integrated Circuit) to perform demultiplexing and readout functions. A step or operation can be implemented to perform the demultiplexing and readout functions.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art, which are also intended to be encompassed by the following claims.

What is claimed is:

1. An electric current imaging system, comprising:
an array of vector magnetometers that senses at least one magnetic field in three directions produced by a flow of electric current on a device, the array of vector magnetometers comprising a MEMS array of vector magnetometer structures configured on an IC (Integrated Circuit) chip; and
a display that displays a visual reconstruction of an original electric current that produces said at least one magnetic field, the display comprising vectors representing direction and magnitude of the original electric current.

2. The system of claim 1 wherein said flow of said electric current is reconstructed at a distance including the magnitude.

3. The system of claim 1 wherein said array of vector magnetometers comprises a plurality of sensing elements.

4. The system of claim 3 further comprising a sensor comprising said array of magnetometers, wherein said sensor communicates data via digital communications.

5. The system of claim 3 further comprising a microcontroller that initializes said plurality of sensing elements.

6. The system of claim 1 further comprising a reconstruction module that visually reconstructs said flow of said electric current on said device from data detected by said array of magnetometers.

7. The system of claim 1 wherein said MEMS array of vector magnetometer structures are configured on a single IC (Integrated Circuit) chip.

8. The system of claim 7 wherein said MEMS array is mated with a CMOS (Complementary Metal Oxide Semiconductor) VLSI (Very Large Scale Integrated Circuit) to perform demultiplexing and readout functions.

9. The system of claim 8 wherein said CMOS VLSI comprises a CMOS readout IC.

10. The system of claim 8 wherein said CMOS VLSI comprise a CCD (Charged Coupled Device).

11. An electric current imaging method, comprising:
sensing, with an array of vector magnetometers comprising a MEMS array of vector magnetometer structures, at least one magnetic field in three directions produced by a flow of electric current on a device; and
displaying a visual reconstruction of an original electric current that produces said at least one magnetic field, the display comprising vectors representing direction and magnitude of the original electric current.

12. The method of claim 11 further comprising reconstructing said flow of said electric current at a distance including the magnitude.

13. The method of claim 11 further comprising configuring said array of vector magnetometers to include a plurality of sensing elements.

14. The method of claim 13 further comprising configuring a sensor to include said array of magnetometers, wherein said sensor communicates data via digital communications.

15. The method of claim 13 further comprising initializing said plurality of sensing elements with a microprocessor.

16. The method of claim 11 further comprising visually reconstructing said flow of said electric current on said device from data detected by said array of magnetometers.

17. The method of claim 11 further comprising mating said MEMS array with a CMOS (Complementary Metal Oxide Semiconductor) VLSI (Very Large Scale Integrated Circuit) that performs demultiplexing and readout functions.

18. The method of claim 17 wherein said CMOS VLSI comprises a CMOS readout IC.

19. The method of claim 17 wherein said CMOS VLSI comprise a CCD (Charged Coupled Device).

20. An electric current imaging system, comprising:
an array of vector magnetometers that sense at least one magnetic field in three directions produced by a flow of electric current on a device, the array of vector magnetometers comprising a MEMS array of vector magnetometer structures configured on an IC (Integrated Circuit) chip;
a CMOS (Complementary Metal Oxide Semiconductor) VLSI (Very Large Scale Integrated Circuit) mated to said MEMS array of vector magnetometer structures to perform demultiplexing and readout functions wherein said CMOS VLSI comprises one of: a CMOS readout IC and a Charged Coupled Device;
a microcontroller that initializes said MEMs array of vector magnetometer structures;
a reconstruction module that visually reconstructs said flow of said electric current on said device from data detected by said array of magnetometers; and
a display that displays said visual reconstruction of said flow of electric current that produces said at least one magnetic field, the display comprising vectors representing direction and magnitude of the original electric current, wherein said flow of said electric current is reconstructed at a distance including the magnitude.

* * * * *